United States Patent
Wang et al.

(10) Patent No.: US 11,019,318 B2
(45) Date of Patent: *May 25, 2021

(54) METHODS TO COMPENSATE MANUFACTURING VARIATIONS AND DESIGN IMPERFECTIONS IN A DISPLAY DEVICE

(71) Applicant: Capso Vision, Inc., Saratoga, CA (US)

(72) Inventors: Kang-Huai Wang, Saratoga, CA (US); Gordon C. Wilson, San Francisco, CA (US)

(73) Assignee: CapsoVision Inc., Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/589,109

(22) Filed: Sep. 30, 2019

(65) Prior Publication Data

US 2020/0045283 A1 Feb. 6, 2020

Related U.S. Application Data

(60) Division of application No. 14/835,497, filed on Aug. 25, 2015, now Pat. No. 10,499,029, which is a continuation-in-part of application No. 14/624,270, filed on Feb. 17, 2015, now Pat. No. 9,307,233, which is a continuation of application No. 11/621,486, filed on Jan. 9, 2007, now Pat. No. 9,007,478.

(51) Int. Cl.
| | | |
|---|---|---|
| *H04N 9/77* | (2006.01) | |
| *H04N 5/217* | (2011.01) | |
| *H04N 5/77* | (2006.01) | |
| *H04N 5/765* | (2006.01) | |
| *H04N 5/365* | (2011.01) | |
| *H04N 5/225* | (2006.01) | |
| *H04N 9/64* | (2006.01) | |
| *H04N 17/00* | (2006.01) | |
| *A61B 1/04* | (2006.01) | |
| *H04N 5/91* | (2006.01) | |
| *H04N 5/85* | (2006.01) | |

(52) U.S. Cl.
CPC ............... *H04N 9/77* (2013.01); *A61B 1/041* (2013.01); *H04N 5/217* (2013.01); *H04N 5/2252* (2013.01); *H04N 5/3651* (2013.01); *H04N 5/765* (2013.01); *H04N 5/772* (2013.01); *H04N 9/646* (2013.01); *H04N 17/002* (2013.01); *H04N 5/85* (2013.01); *H04N 5/91* (2013.01)

(58) Field of Classification Search
CPC ........ H04N 9/77; H04N 5/3651; H04N 5/772; H04N 5/217; H04N 5/765; H04N 5/2252; H04N 9/646; H04N 17/002; H04N 5/91; A61B 1/041
See application file for complete search history.

(56) References Cited

U.S. PATENT DOCUMENTS

| | | | |
|---|---|---|---|
| 2005/0078204 A1 | 4/2005 | Matsuoka et al. | |
| 2013/0016138 A1* | 1/2013 | Sasaki | G09G 3/3648 345/690 |
| 2014/0055473 A1* | 2/2014 | Kikuchi | G09G 5/393 345/531 |

* cited by examiner

*Primary Examiner* — Ahmed A Berhan
(74) *Attorney, Agent, or Firm* — Blairtech Solution LLC

(57) ABSTRACT

A display device includes (a) a non-volatile memory containing corrective data for compensating input image data received; (b) display hardware receiving control and data signals for displaying an image; and (c) an image processing circuit that retrieves the corrective data from the non-volatile memory to generate the data signals for the display hardware, after applying the corrective data to each color component of each pixel in the input image data.

21 Claims, 9 Drawing Sheets

METHODS TO COMPENSATE MANUFACTURING VARIATIONS AND DESIGN IMPERFECTIONS IN A DISPLAY DEVICE

CROSS-REFERENCE TO RELATED APPLICATIONS

The present application is a divisional application of U.S. patent application Ser. No. 14/835,497, entitled "Methods to Compensate Manufacturing Variations and Design Imperfections in a Display Device", filed Aug. 25, 2015, which is a continuation-in-part application of co-pending U.S. patent application Ser. No. 14/624,270, entitled "Methods to Compensate Manufacturing Variations and Design Imperfections in a Capsule Camera," filed Feb. 17, 2015, which is a continuation of U.S. patent application Ser. No. 11/621,486, entitled "Method to Compensate Manufacturing Variations and Design Imperfections in a Capsule Camera," filed on Jan. 9, 2007, now granted as U.S. Pat. No. 9,007,478, issues Apr. 14, 2015.

BACKGROUND OF THE INVENTION

1. Field of the Invention

The present invention relates to methods for compensating for variations in a manufacturing process. In particular, the present invention relates to applying such methods to optical instruments.

2. Discussion of the Related Art

The capsule camera has proved to be an effective minimally-invasive way for examining the gastrointestinal (GI) tract. One example of a swallowable capsule camera is described in the U.S. Pat. No. 5,604,531, issued to the Ministry of Defense, State of Israel. A number of patents assigned to Given Imaging describe in greater detail a capsule camera system which uses a transmitter to send images captured by the camera to an external receiver. Other capsule camera examples include U.S. Pat. Nos. 6,709,387 and 6,428,469.
There are also other patents to the Olympus Corporation regarding capsule cameras. For example, U.S. Pat. No. 4,278,077 discloses a film camera in a capsule designed for the stomach. U.S. Pat. No. 6,939,292 discloses a capsule camera with a buffering memory and a transmitter. U.S. Pat. No. 6,800,060 discloses a capsule camera which stores image data in an atomic resolution storage (ARS) device.

Various advancements in electronics may now be incorporated into the capsule camera. For example, an LED provides a compact and low-power lighting source. CMOS image sensors reduce the component count and power. The further miniaturizing of integrated circuit geometry allows SOC (system-on-a-chip) techniques to be used, which reduce the size and power of the capsule camera. However, size reduction pushes the limits of manufacturing tolerances. For example, manufacturing processes for semiconductor image sensors inherently include not only lot-to-lot, wafer-to-wafer, and die-to-die variations, but also pixel-to-pixel variations within a die. Even the analog circuits sensing the charge stored in a cell to provide digital image data vary from location to location within a die. In addition, LEDs are known for variations in their light spectrum and intensity. Also, because the center of a lens passes light better than at the edge, a higher intensity results in the center of the image than at the edges. There are also variations from lens to lens, even if the lenses are fabricated from the same mold.

Another example results from the fact that illumination sources in a capsule camera illuminate objects only a few centimeters away, the objects receive non-uniform light intensities. Moreover, the transparent window provided in the capsule housing for the LED light to pass through is not perfectly transparent. Thus, when the light sources in the capsule (e.g., LEDs) are turned on, the transparent window reflects some of the light within the camera's field of view back to the light sources and the image sensor.

As the capsule camera is intended to allow a physician to examine the inside of a patient's GI tract, its accuracy and image quality are of paramount concern.

SUMMARY

According to one embodiment of the present invention, a display device includes (a) a non-volatile memory containing corrective data for compensating input image data received; (b) display hardware receiving control and data signals for displaying an image; and (c) an image processing circuit that retrieves the corrective data from the non-volatile memory to generate the control and data signals for the display hardware, after applying the corrective data to each color component of each pixel in the input image data.

According to one embodiment of the present invention, the corrective data in the non-volatile memory is generated from a calibration step during manufacturing by a diagnostic system detecting an intensity of each color component in each pixel of the display hardware. The calibration provides corrective data which enables compensation to the input image data over a range of intensities for each color component of each pixel displayed by the display hardware.

According to one embodiment of the present invention, the display device further includes a thermometer for measuring an operating temperature in the display hardware. In that embodiment, the corrective data enables compensation of the input image data based in part on the measured temperature.

According to the present invention, the corrective data may be stored in any suitable format. For example, in one embodiment, the corrective data is stored in the non-volatile memory in a table format. The corrective data in that case may correspond to the corrected values for replacing corresponding values in the received input image data. Alternatively, the corrective data may correspond to compensation values to be applied to corresponding values in the received input image data. As another example, the corrective data may correspond to corrective values for predetermined values of input image data. In that case, corrective values for the received input image data are interpolated or extrapolated from the corrective values for the predetermined values. As one further example, the corrective data may correspond to corrective values for predetermined values of input image data and values of parameters of a model. In that example, corrective values for the received input image data are generated from the values of the parameters based on the corrective values for the predetermined values.

According to one embodiment of the present invention, the corrective data may correspond entirely to values of parameters of a model from which corrective values are generated based on the corresponding received input image data. The model may be any suitable function, such as a linear function or polynomial function.

According to one embodiment of the present invention, the stored corrective data includes only corrective values that are each applicable to one of a number of specific groups of neighboring pixels in the image hardware. In that case, each corrective value is applied to each pixel of the corresponding group of neighboring pixels.

The present invention is applicable to correcting manufacturing variations in the digital domain, as well as the analog domain.

According to one embodiment of the present invention, a method for correcting input image data received into a display device for manufacturing variations includes (a) generating corrective data from a calibration step during manufacturing by a diagnostic system detecting an intensity of each color component of each pixel of display hardware in the display device; (b) storing the corrective data into a non-volatile memory in the display device; and (c) at a subsequent time, (i) retrieving the corrective data from the non-volatile memory; (ii) applying the corrective data to correct each color component of each pixel in the received input image data; and (iii) generating the control and data signals for the display hardware, based on the corrected input image data.

The present invention finds application not only in capsule cameras. The present invention is applicable to cameras and display devices, in general.

The present invention is better understood upon consideration of the detailed description and the accompanying drawings.

DETAILED DESCRIPTION OF THE INVENTION

Figure 1:
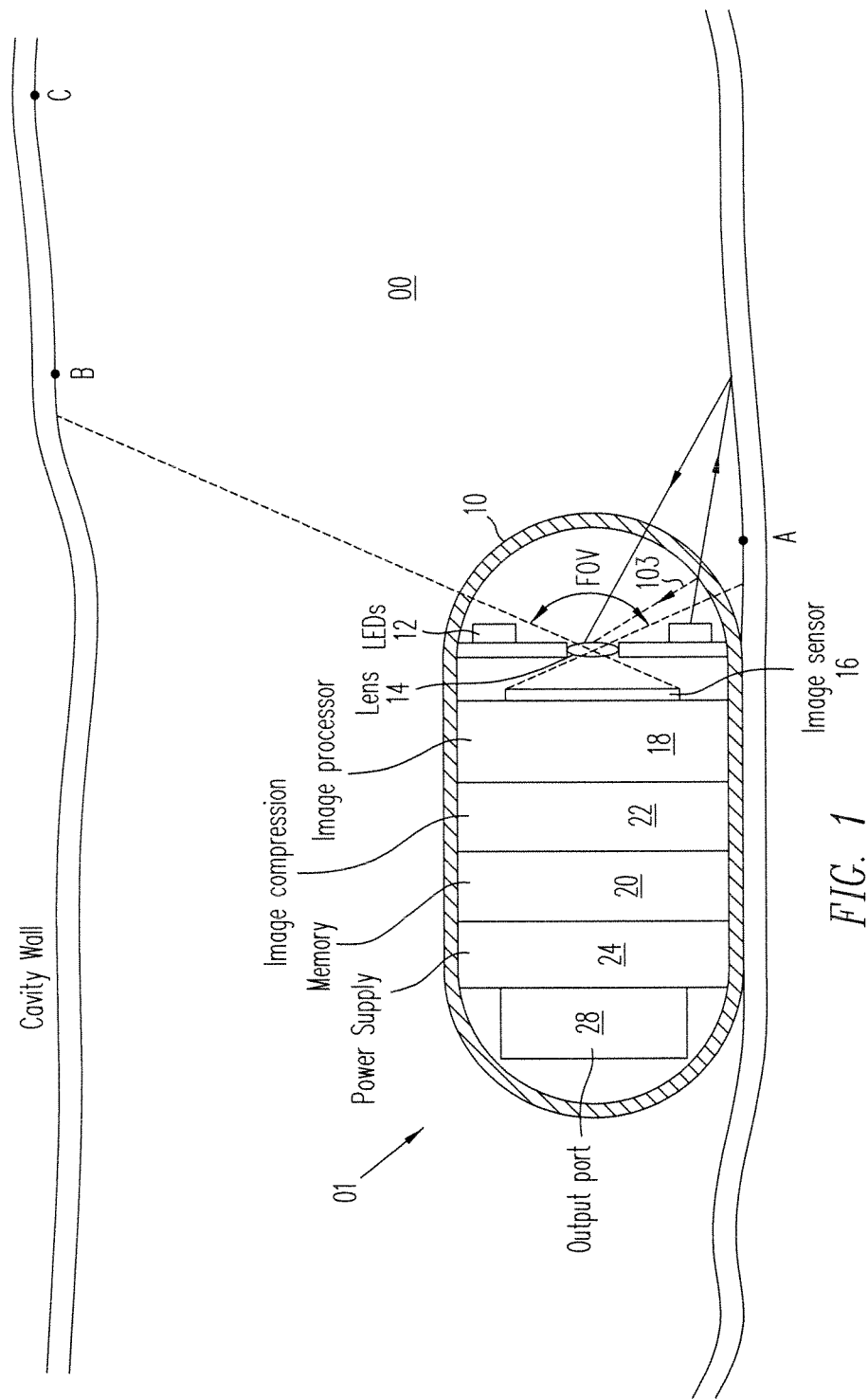
FIG. 1 shows an example of a capsule camera in the GI tract.

FIG. 1 shows an exemplary capsule camera in the GI tract. As shown in FIG. 1, swallowable capsule camera system 01 is seen inside body lumen 00, which may be, for example, the colon, the small intestines, the esophagus, or the stomach. Capsule camera system 01 is entirely autonomous while inside the body, with all of its elements encapsulated in a capsule housing 10 that provides a moisture barrier, protecting the internal components from bodily fluids. Capsule housing 10 includes at least a transparent window, so as to allow light from the light-emitting diodes (LEDs) of illuminating system 12 to pass through the wall of capsule housing 10 to illuminate the walls of lumen, and to allow the scattered light from the lumen 00 walls to be collected and imaged within the capsule camera. Capsule housing 10 also protects lumen 00 from direct contact with the foreign material inside capsule housing 10. Capsule housing 10 is provided a shape that enables it to be swallowed easily and later to pass through the GI tract efficiently. Generally, capsule housing 10 is sterile, made of a non-toxic material, and is sufficiently smooth to minimize the chance of lodging within the lumen.

As shown in FIG. 1, capsule camera system 01 includes illuminating system 12 and a camera that includes optical system 14 and image sensor 16. An image captured by image sensor 16 may be processed by image processor 18, which performs various image processing functions, such as determining whether or not the capsule is moving relative to the portion of the GI tract within the optical view of the camera. Image processor 18 may be implemented by a digital signal processor (DSP) or a central processing unit (CPU). Image processor 18 may have one or more partial frame buffers. A semiconductor non-volatile archival memory 20 may be provided to allow the images to be retrieved throughout output port 28 at a docking station or workstation outside the body, after the capsule is recovered. The image in archival memory 20 may be stored in a compressed form, using data compression module 22. (Data compression module 22 may be implemented in hardware, or in software running on image processor 18). Capsule camera system 01 is powered by battery power supply 24. Capsule camera system 01 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. In one embodiment, white LEDs may be formed by various components, such as a blue LED or a violet LED, along with phosphorescent materials that are excited by the LEDs' light to emit light at longer wavelengths. The portion of capsule housing 10 that allows light to pass through may be made from bio-compatible glass or polymer.

Optical system 14, which may include multiple refractive, diffractive, or reflective lens elements, provides an image of lumen 00 within its field of view on image sensor 16. Image sensor 16 may include charged-coupled devices (CCD) or complementary metal-oxide-semiconductor (CMOS) type sensor devices that convert the received light intensities into corresponding electrical signals. Image sensor 16 may have a monochromatic response or include a color filter array to allow a color image to be captured (e.g. using the RGB or CYM color space representations). The analog signals from image sensor 16 are preferably converted into digital form to allow use of digital processing techniques. Such a conversion may be accomplished using an analog-to-digital (A/D) converter inside image sensor 16 (as in the current case), or at another location inside capsule housing 10. The A/D unit may be provided between image sensor 16 and the rest of the system. LEDs in illuminating system 12 are synchronized with the operations of image sensor 16. One function of control module 26 (not shown) is to control the LEDs during image capture operation.

Image processor 18 may select an image to retain when the image shows enough motion relative to a previous image in order to conserve the limited storage space available. The captured images may be stored in on-board archival memory system 20. Output port 28 shown in FIG. 1 is not operational in vivo, but uploads data to a workstation after the capsule camera is recovered from a journey through the body.

When the LEDs are turned on, their light passes through the transparent window in capsule housing 10 to illuminate objects in the GI tract. The reflected light from these objects passes through the transparent window and reaches lens 14, which focuses the image on imaging sensor 16. Some of the light emitted from the LEDs is reflected back from the surface of the transparent window, as shown in long-short dash line 103, through lens 14 onto image sensor 16. Because every pixel in a cell array in image sensor 16 is in some sense unique, image sensor 16 may be characterized under a uniform lighting condition provided externally—with the LEDs in capsule camera system 01 turned off—to determine pixel-to-pixel variations in image sensor 16. In fact, the different readouts of these pixels represent both the pixels' variations and the lens' contribution to non-uniform pixel values.

Figure 2:
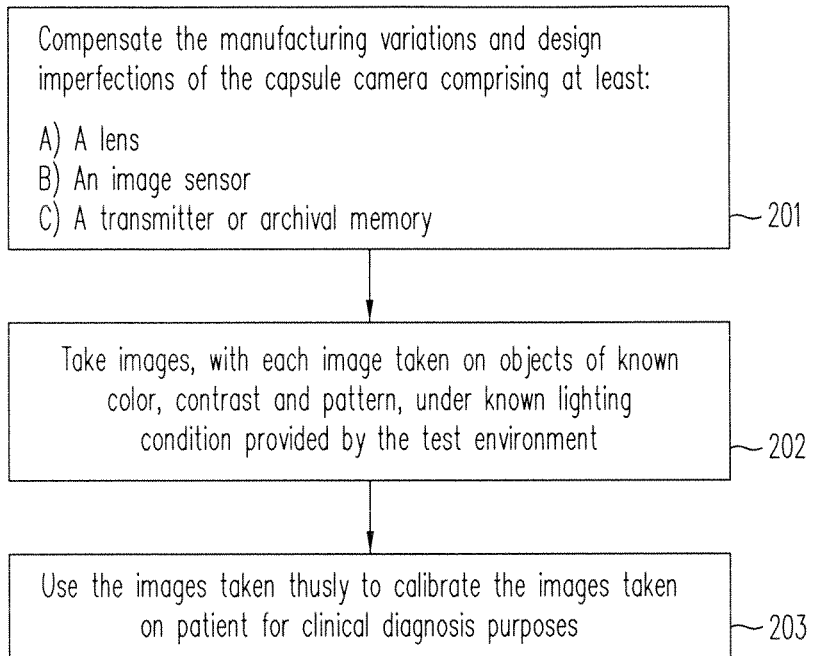
FIG. 2 illustrates a method for characterizing pixel-to-pixel variations and design imperfection in a capsule camera, in accordance with one embodiment of the present invention.

FIG. 2 illustrates a method for characterizing pixel-to-pixel variations and design imperfections in a capsule camera, in accordance with one embodiment of the present invention. As shown in FIG. 2, a capsule camera including at least a lens system, an image sensor and a transmitter or an archival memory is prepared (step 201). Next, at step 202, objects illuminated by light of a known color, intensity, contrast or pattern is placed in the field of view of the lens system and exposures are made. These images are then used to characterize or calibrate the capsule camera system. The images may be stored in the archival memory or transmitted. At a subsequent time (step 203), these images are used to calibrate the images captured from a patient for clinical diagnosis purposes.

One method for compensating variations in pixel responsivity and the field dependence on the camera's response (i.e., the non-uniformity in sensor illumination, even in the presence of a uniform object illumination) is to present the camera with a field of uniform color and brightness during calibration. A test image is then taken under this illumination condition and used to obtain an average value AR for the red component of all pixels. If a particular pixel's red component signal is $PR_i$, the red component of this pixel may be compensated during normal operation by multiplying the red component of the measured pixel value by a factor $A_R/PR_i$. Other color components may be compensated in a like manner. (This method may also be applied likewise to color components in other color space domains).

Figure 3:
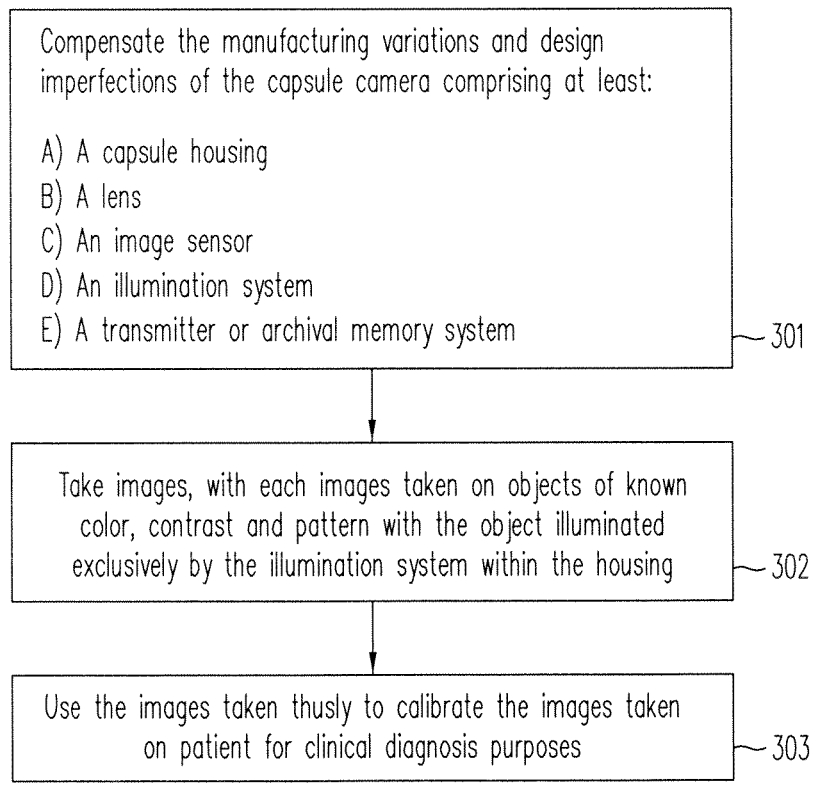
FIG. 3 illustrates a method for characterizing pixel-to-pixel variations and design imperfection in a capsule camera under its own illumination, in accordance with one embodiment of the present invention.

Characterization of the capsule camera system under its own illumination (e.g., illumination system 12) may be carried out. FIG. 3 illustrates a method for characterizing pixel-to-pixel variations and design imperfection in a capsule camera under its own illumination, in accordance with one embodiment of the present invention. The "white balance" of the combined illumination and imaging system can be corrected. As shown in FIG. 3, a capsule camera including at least a lens system, an image sensor, an illumination system within the capsule camera's housing, and a transmitter or an archival memory is prepared (step 301). Next, at step 302, objects of known color, contrast, and pattern are illuminated by the illumination system in the field of view of the lens system and exposures are made. These images are then used to characterize or calibrate the capsule camera system. The images may be stored in the archival memory or transmitted. At a subsequent time (step 303), these images are used to calibrate the images captured from a patient for clinical diagnosis purposes.

During calibration, images may be taken of various colored fields. The average red, green, and blue pixel responses for each test field can be compared to an ideal responses and correction factors determined. For example, if a measured average value for the red component is $A_R$ and the expected average pixel value is $A_R^E$ then the factor $A_R^E/A_R$ may be used to correct color fidelity—by multiplying each pixel in a measured image by this factor. Similar factors may be derived for the green and blue components. Different test color fields may yield different calibration factors for the three primary colors. Alternatively a white field may be used to calibrate all colors. Multiple images of the same test pattern may be taken and the results averaged so that time-dependent noise is reduced in the measured pixel values. A weighted average of calibration factors over the test conditions can be determined and stored for later image correction. The compensation factors can be stored in capsule the camera system 01, in the data recorder, or in the workstation software. The compensation factors may each be defined using an equation, a curve, a piecewise curve or a lookup table. The number of parameters per pixel may also be more than one.

Within image sensor 16, each pixel value is also affected by effects not relating to light input. Such effects may be seen in an output value of a "dark" pixel. A dark pixel may be a pixel not within the field of view of the optical system 14 and which is typically covered by an opaque material. An output value of such a pixel is not attributed to light input, but effects such as thermally-induced charge leakage. An operational pixel may be compensated by adding as an offset the thermally-induced leakage current measured at a dark pixel (or the average thermally-induced leakage current of a group of dark pixels). The thermally-induced leakage current is a function of both temperature and time. The temperature of a capsule camera in operation is expected to be relatively fixed at the human body temperature, plus a few degrees determined by both the power consumption of the capsule camera and the thermal conductance. As a first-order estimate, the thermally-induced leakage current is proportional to the time between a pre-charge of the pixel and the readout.

The pixel-to-pixel variations or non-uniform pixel responsivity, including the effects of lens system 14, may be compensated according to the following equations (1) for the R, G and B color components, respectively:

$$R = F_R \times P_R + C_{1R} \times t_1 + C_R$$

$$G = F_G \times P_G + C_{1G} \times t_1 + C_G \quad (1)$$

$$B = F_B \times P_B + C_{1B} \times t_1 + C_B$$

where, $P_R$, $P_G$, and $P_B$, are the measured component values for the three color components read from a pixel in image sensor 16, $F_R$, $F_G$, and $F_B$ are multiplication factors provided for correcting pixel-to-pixel variations and for adjusting the average pixel value, and $C_R$, $C_G$ and $C_B$ are offsets—which may be positive or negative—for each pixel. In this model, the pixel response is assumed to be linearly dependent on the received radiant energy absorbed by the pixel. The slope of the linear dependency is the "responsivity." At a dark pixel (i.e., at zero input radiant energy), the zero-light response ("dark current") represent an offset. It is convenient to use multiplicative factors for compensation because of its simplicity. However, if the pixel characteristics are non-linear with respect to the component values, a more sophisticated compensation function may be required. In the general case, the term $F_k \times P_k$, k=R, G, B may be replaced by $f_k(P_k)$). Such a function may be, for example, a polynomial, or a function that includes logarithmic or exponential terms. Of course, $f_k(P_k)$ may also be a function of other parameters—such as temperature, as discussed below. R, G, and B are the primary colors. $P_R$, $P_G$ and $P_B$ are non-negative values (each value is clamped to zero, when its calculated value is negative, or clamped to $2^N-1$ for N bit resolution, when the calculated value exceeds $2^N-1$).

Parameters $C_{1R}$, $C_{1G}$ and $C_{1B}$ are provided to compensate for the thermally-induced leakage current. The contribution of the leakage current to each color component is proportional to time $t_1$, which is the time duration between cell pre-charge and cell readout. In order to solve for $F_R$, $C_{1R}$, and $C_R$, three test images must be taken that include two different illumination intensities and two different values of $t_1$. This leakage current may be calculated either in the capsule camera or outside the capsule camera. For calculation outside the capsule camera, the timing parameters for each image are stored in the flash memory or transmitted by wireless. The memory space needed to store these timing parameters is miniscule relative to the size of the image. In the above discussion, although an RGB space is used merely for illustrative purposes other color spaces may also be used.

The data for each color component is read out. As a first-order estimate—i.e., without compensating for thermally-induced leakage current, discussed below—two parameters $F_i$ and $C_i$ may be stored or transmitted for each color component R, G or B. Raw color image data may also be stored or transmitted to reduce the space requirement or transmission power. These raw color image data may correspond to a small number of images of red, blue, and green objects illuminated at different intensities. Alternatively, images of a number of objects each with a uniform known color may be used to derive these coefficients. For example, lighting conditions in which the same RGB ratio is used, but different intensities are provided may be used to solve for the $C_R$, $C_G$ and $C_B$ parameters.

Because both the dark current and the responsivity vary from pixel to pixel, the values of these parameters are calculated for each pixel, and compensation is applied to each pixel according the values of the parameters associated with the pixel. Alternatively, compensation may be provided for each pixel in a block of pixels, using the same parameter values (e.g., the same additive and multiplicative factors) calculated over the pixels of the entire block. A block may be any group of pixels, not necessarily pixels over a rectangular area of the image.

The inventors also recognize that the method of the present invention is applicable also to cameras used for applications other than as a capsule camera operating under body cavity conditions. For these other applications, the temperature dependences in $C_{1R}$, $C_{1G}$ and $C_{1B}$, $C_R$, $C_G$ and $C_B$, and multiplicative factors $F_R$, $F_G$, and $F_B$ (or their functional forms), may have to be taken into consideration. In one embodiment, for example, measurements are taken at multiple temperatures. At each temperature, the values of $F_k$ (or its functional form), $C_{1k}$, and $C_k$, k=R, G, or B are solved according to the procedure described above.

As discussed above, to make compensation available during operations, the coefficients may be calculated for each pixel at the time of manufacture and stored. Alternatively, the images data taken under known uniform illumination conditions may be stored for subsequent calculations of the coefficients. As the number of images taken during operations in a capsule camera is in the order of tens of thousands, the data storage requirement for a few or even a few tens of test images for characterization is minimal, and may be stored in the on-board archival memory (e.g., memory 20). These test data may also be transmitted by wireless to an external recorder, which may be used later in a physician's examination of the images. Each capsule camera may be provided an identification number (ID). Based on the ID, the test data may be provided on and downloaded from a website at the time the physician examines the captured image data.

The computational requirement (e.g., in terms of circuit area and power) for extracting the coefficients based on the simple relationships discussed above is relatively low and, either the test image data (e.g. values for each color component) or the coefficients, which may be calculated by on-board circuits, may be easily stored or transmitted. To illustrate the power and circuit requirements, consider an order-of-magnitude estimate for a JPEG circuit required to process thirty 300 k resolution images. (There are many selections of JPEG circuits available from various popular foundries' libraries, each consisting of no more than about 50 k gates.) For a 0.09 gm process, the average intrinsic gate capacitance is estimated to be:

$$4C_iWL \approx (5\mathit{ff}/\mu m^2)(0.5\mu m)(0.09\mu m + 0.2\mu m) \approx 3\mathit{ff}$$

(The factor of 4 assumes that an equivalent gate has 4 transistors.) The 0.2 μm term represents fringing capacitance. For a one-clock-per-code-word JPEG standard widely adopted today, about 30 MHz is needed to run a thirty frames per second real time speed. Therefore, assuming a wiring capacitance of twice the intrinsic capacitance and an activation rate of ⅓ of all circuits, the power required is estimated to be:

$$0.5CV^2*30 \text{ MHz} = 0.5*(2+1)*3\mathit{ff}*50k*(\tfrac{1}{3})*(1V)^2*30 \text{ MHz} = 2.25 mW$$

The energy for processing 30 frames is 2.25 mW×1 sec=2.25 mJ, which is a miniscule value within the capability of the batteries of the capsule camera. By comparison, the equations for calculating the compensation coefficients above are much simpler than the computational requirements for JPEG processing, which includes space-frequency domain discrete cosine transform (DCT) operations and entropy encoding, among other steps specified in ISO 10918-2 JPEG coding standard. Further, the number of test images required for characterization is normally substantially less than 30 images. Therefore, extracting the coefficients in the capsule camera itself may also be easily achieved in practice.

Thus, the cost of correcting the captured images using the methods discussed herein, and other methods are not cumbersome operations. In addition, both the compression ratio and the quality of the compressed image are more favorable in a corrected image than an uncorrected image because the pixel-to-pixel variations in the uncorrected image are presented as noise in the image data. Without an elimination procedure, such noise is blended in with the useful information and, consequently, increases the number of the bits in a compressed image. The short range differences (e.g., between adjacent pixels) increase the frequency-domain data, thus impacting both the compressed file size and the image quality. During compression, the processing of the noise in the image data further increases power consumption. For example, in the case of MPEG processing, a previous reference frame has to be decompressed in order to code differences between the current frame and a reference frame. The long range differences (i.e., between pixels a substantial distance away from each other within the sensor array) affect motion estimation in MPEG-like compression. Motion estimation in such a compression algorithm is affected by both short range differences and long range differences, because the compression is carried out by space- and frequency-domain transformations after motion estimation.

A method of the present invention is applicable to characterizing image sensors outside of the camera. Such a method achieves better quality, a better compression ratio and provides a lesser power requirement, because the method introduces less noise, allows better matching, and results in less frequency domain terms. The impact on MPEG compression is two-folds: both short-range and long-range variations are corrected. The corrections improve compression ratio of short-range, adjacent or proximal pixels within a sensor, with the long-range pixel-to-pixel variations higher than the short-range variations by an order of magnitude. The camera's objective optical elements may also be separately characterized. Typically, each individual objective optical element need not be separately measured. The calibration data for the image sensor and the objective optical elements may be combined.

In one embodiment of the present invention, an image sensor is characterized using one of the methods discussed above (with or without providing a lens and under uniform or known conditions). An image sensor typically has more high frequency components due to compression noise. If a lens is provided, a nearly ideal' lens should be used. Otherwise, the lens should be optically characterized offline before use, with its imperfections taken into account. Correction data is then derived, which is then associated with the particular sensor. The correction data may then be provided to the camera manufacturer for subsequent use.

Light from the illumination sources are, to some extent, reflected by the inner and outer surfaces of capsule housing 10 and other objects within capsule housing 10 (e.g., particulate contamination). Such reflections may be both specular and scattered. Some reflected light may pass into the camera's input pupil to collect on the image sensor. Light may reflect multiple times from multiple objects before reaching image sensor 16.

The spurious signals resulting from reflections of the LED light are independent of the scene photographed. To characterize the reflected illuminating light picked up by image sensor 16 from the surface of the transparent window in capsule housing 10, the capsule camera may be placed completely in a light-absorbing environment (i.e., no light reflects from the environment). Under this arrangement, the light sensed at image sensor 16 consists only of the light emitted from the LEDs that is reflected from capsule housing 10 or from other objects within the capsule. For simplicity, the following discussion assumes LED light sources but other light sources could be used instead, such as those based on incandescence, fluorescence, field-ionization, phosphorescence, or any other light emission process.

The measured red, green, and blue pixel signals may be expressed as, $$P_R = \sum_{i=1}^{n} C_{ir} I_i t_{LEDi} - C_{lR} t_l - C_R \quad (2)$$

-continued $$P_G = \sum_{i=1}^{n} C_{ig} I_i t_{LEDi} - C_{lG} t_l - C_G$$

$$P_B = \sum_{i=1}^{n} C_{ib} I_i t_{LEDi} - C_{lB} t_l - C_B$$

where $C_{1r}, \ldots C_{nr}, C_{1g} \ldots C_{ng},$ and $C_{1b}, \ldots C_{nb}$ are parameter relating to the intensity of each LED, $I_1, \ldots, I_n$ are the currents in $LED_1$ to $LED_n$, respectively, and times $t_{LED1}, \ldots, t_{LEDn}$ are the durations of the corresponding LED currents. The subtractive terms such as $C_{1R}$ and $C_R$ are respective leak parameter and offset determined using the previously described procedures. Since the LED emitted optical power is roughly linear with current, the reflected light sensed at the image sensor is expected to depend linearly on the currents flowing in individual LEDs integrated over time. For simplicity, equations (2) assume the current L, for LED' is constant but the current terms in equations (2) may also each be expressed as an integral of the instantaneous current over time, rather than multiplication of current and time.

Measurements are made with n different combinations of LED currents to allow solving the n independent linear equations for each color. Ideally, each LED is turned on by itself in turn. The n equations for red may be solved using n images, and the values of leakage current factor, $C_{1R}$, and offset $C_R$ obtained from the image tests of equations (1). Alternatively, two additional images may be taken and, using equations (2), the leakage current and offset factors may be obtained. In that case, the number of total images needed is n+2.)

The reflections from the outer surface of capsule housing 10 depend on the medium in which the capsule camera is immersed. Often, in the GI tract, the capsule is immersed in a watery liquid. In some cases, the capsule will be only partially covered in liquid. One set of calibration data of LED reflections may be taken with the capsule in a black container filled with water. Another set of calibration data may be taken without water. When the GI image data are corrected, the calibration data set which provides optimal correction can be selected. A different set of calibration data may be selected to correct a different image region. The suitable correction for an image region may be indicated by various criteria such as:
1. Minimize high frequency components of spatial frequency spectrum.
2. Minimize sharp edges in the image, using image processing algorithms for detecting edges.
3. Maximize change between successive images. Usually, the medium touching the capsule within an image region is the same from one frame to the next, so that the suitable correction in each pixel for LED reflections off the capsule housing 10's outer surface is invariant from one frame to the next. If the correction is correctly identified (i.e., using the proper calibration data set), the change in image is maximized.
4. Yield only non-negative corrected pixel signals. A negative value indicates that the wrong calibration data set is applied.

The uniqueness of each LED and the non-uniform light that is cast on objects by the LEDs—due to both their respective positions and the finite distances between the objects and the light sources—may also be compensated. Even without knowing the distances inside the small intestines and inside the large intestine, a correction may still be made since the light sources' locations and strengths are known and an average human being's intestines have certain characteristic range in shape and size.

Tests or characterizations designed to extract the compensation parameters may be carried out during the manufacturing process (e.g. during the assembly process), storing the resulting images and the associated information or derived coefficients inside the capsule camera or externally.

Alternatively, the characterization or test may be performed by a hospital technician or by a physician, who runs an automatic test program with the capsule camera placed into a container providing the controlled characterization environment. The test images with associated information or extracted coefficients may be stored in an on-board memory or, if the capsule camera has a wireless transmitter and an antenna, the coefficients database or the images with associated information may be transmitted outside. These data may be retrieved at a later time at a workstation for display and archiving. The characterization data may be archived with a patient's health record or with the raw (i.e., uncorrected) image data. Alternatively, the corrected image and the characterization data are stored, with a description of how the compensation procedures are carried out. The physicians may have the freedom to undo the compensation using the characterization data.

Figure 4:
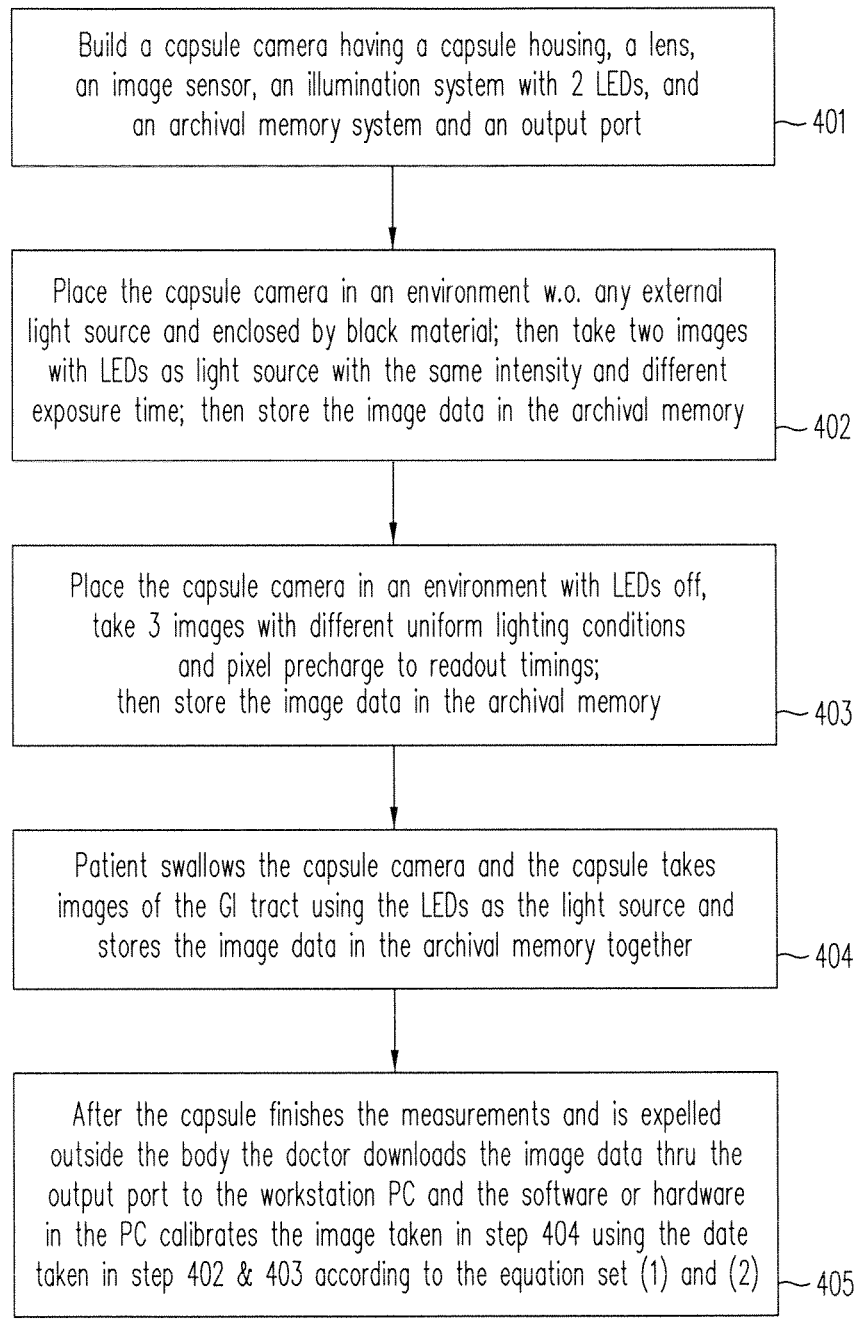
FIG. 4 shows a method for using a capsule camera using the characterization procedures described above, in accordance with one embodiment of the present invention.

FIG. 4 shows a method for using a capsule camera using the characterization procedures described above, in accordance with one embodiment of the present invention. As shown in FIG. 4, a capsule camera including at least a lens system, an image sensor, an illumination system with two LEDs inside the capsule housing, an archival memory and an output port is prepared (step 401). Next, at step 402, the capsule camera is placed in a light absorbing environment without external light sources. Two images are then taken using illuminations by the illumination system at different relative illuminations. (The term "relative illumination" refers to the product of exposure time and light intensity.) The images are then stored in the archival memory. At step 403, the capsule camera is placed in an environment of uniform lighting condition using an external lighting source. Three images of different uniform lighting conditions and pixel precharge to readout times are captured. The images are then stored in the archival memory.

Alternatively, at step 402, images are taken each with one LED on by itself in a dark environment. Then, two images are then taken with both LEDs off for two different time periods. The time-dependent and time-independent leakage signals as well as the LED reflections are characterized. The characterization data is then stored in the archival memory. Then, at step 403, one or more images are taken with a uniform white background and not LED illumination. (Only one image is required to determine responsivity.)

At step 404, the capsule camera is swallowed by a patient to take images of the patient's GI tract, using the capsule camera's illumination system as light source. These images are captured into the archival memory system. At step 405, after the capsule camera is expelled from the patient's body, the capsule camera is recovered, and the captured image and the images taken at steps 402 and 403 (if stored) are retrieved through the output port of the capsule camera. The images taken at steps 402 and 403 are used to extract the parameter values in accordance with equations (2) and (1), respectively, for characterization or calibration of the capsule camera system. The captured images are then compensated using the extracted parameter values.

Figure 5:
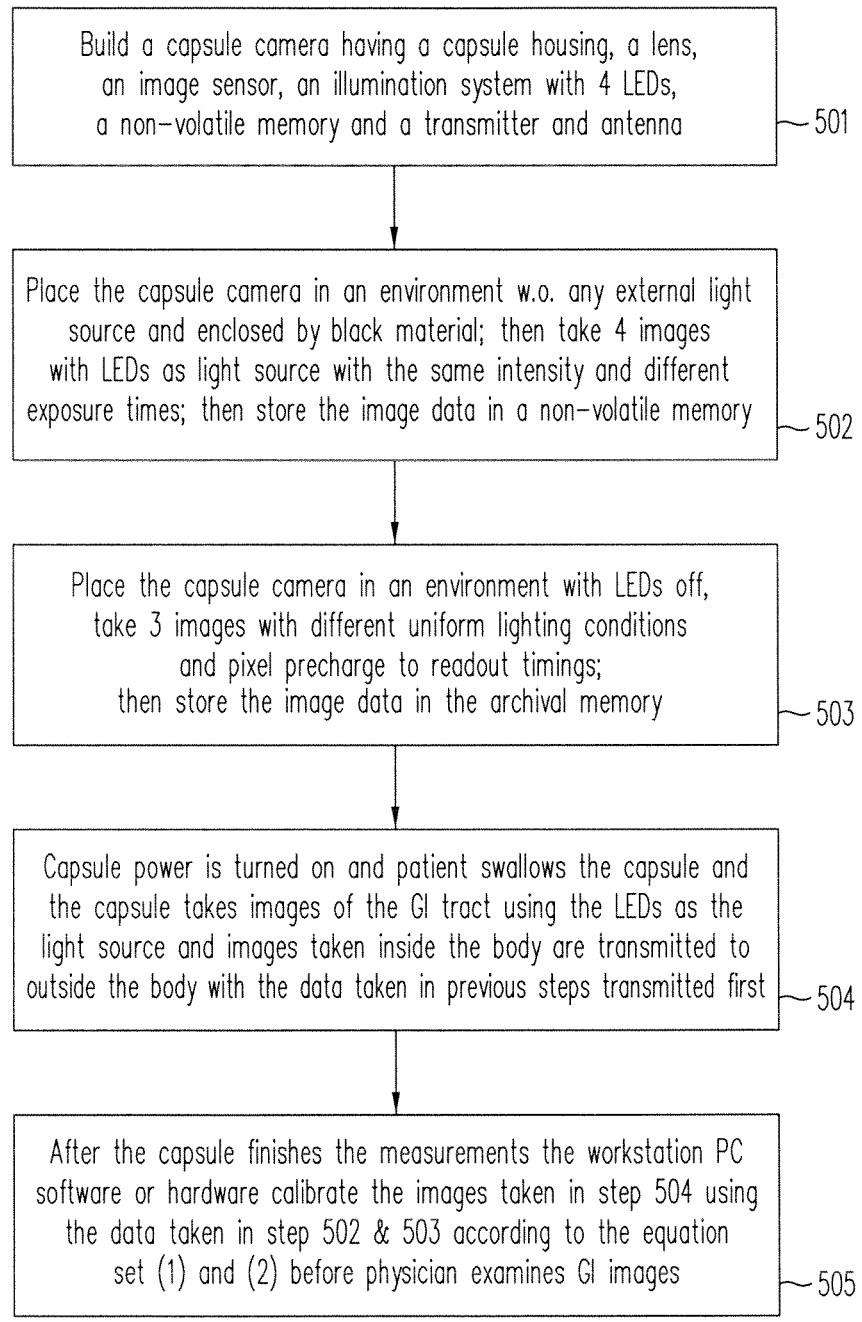
FIG. 5 illustrates an alternative embodiment of the present invention described in conjunction with FIG. 4.

Alternatively, the test or characterization data may be transmitted through an output port (e.g., output port 28) or transmitted by wireless means to outside the capsule camera for external storage. FIG. 5 illustrates an alternative embodiment of the present invention described in conjunction with FIG. 4. In the method illustrated in FIG. 5, instead of an archival memory, the capsule camera is provided with a non-volatile memory buffer and a transmitter. The images taken in the capsule camera, including the images taken at steps 502 and 503, are first stored in non-volatile memory buffer and transmitted to an external receiver, where the images are stored for use in the subsequent steps. In one embodiment, the stored correcting image data or the coefficients are transmitted to the receiver wirelessly just before the capsule takes measurements of the patient.

The capsule camera may be marked with an ID and the externally stored test data or the parameters extracted from the test data, may be made available on websites, by e-mail, in a flash memory, on a VCD or another means. In one embodiment, after the capsule camera is recovered from traversing the GI tract, the measurements data may be downloaded to a workstation, where the test data, or the parameters extracted from the test data, may be retrieved to compensate the captured image data. Alternatively, an ID or ID information may be embedded in the test or characterization image or coefficient data. A technician at a workstation may use the embedded ID to retrieve the test or characterization data or coefficients over the internet, or from another storage media, to perform compensation.

Figure 6:
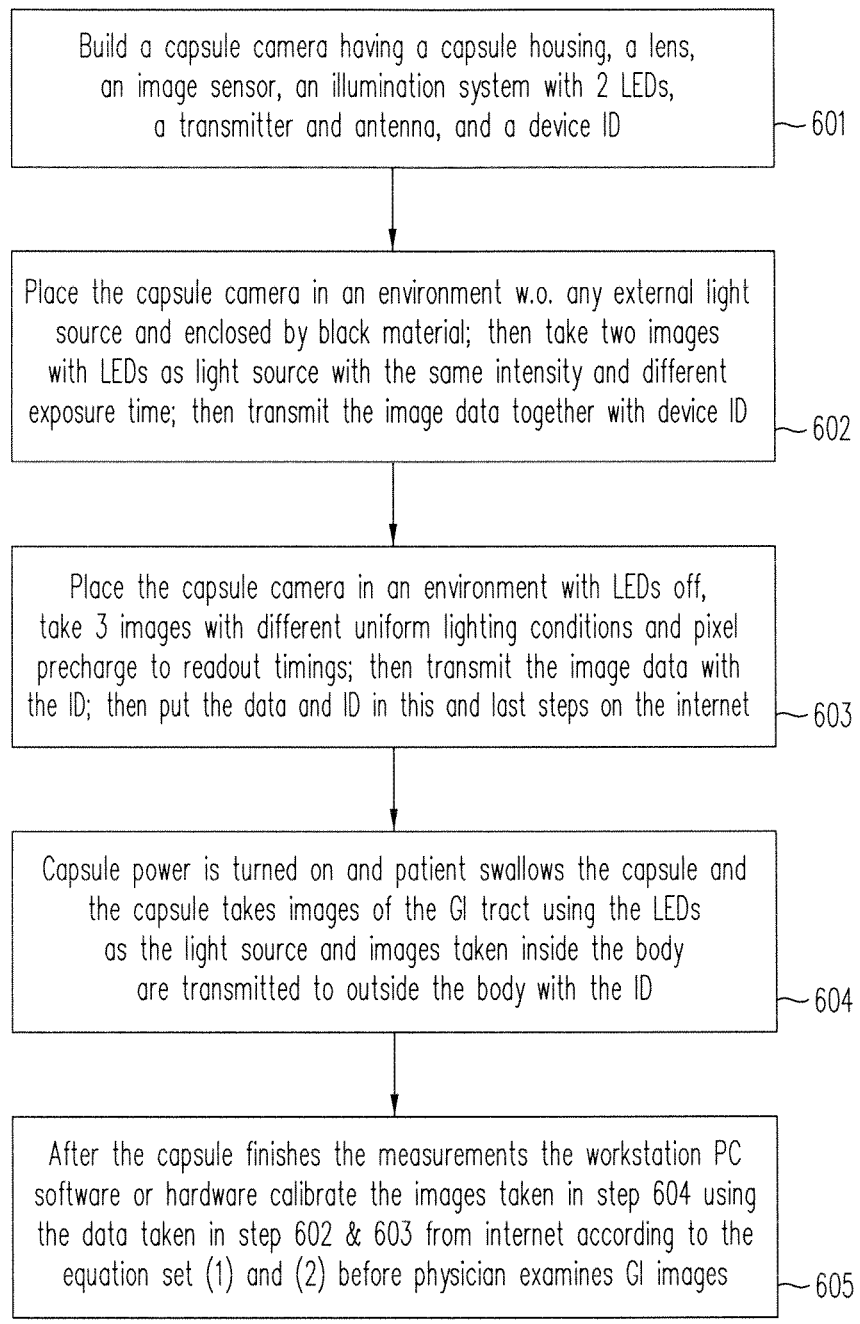
FIG. 6 illustrates an alternative embodiment of the present invention described in conjunction with FIG. 4.

FIG. 6 illustrates an alternative embodiment of the present invention described in conjunction with FIG. 4. In the method illustrated in FIG. 6, instead of an archival memory, the capsule camera is provided with device ID and a transmitter and antenna. The images taken in the capsule camera, including the images taken at steps 602 and 603, are transmitted to an external receiver together with the device ID. The images are stored at an external depository, which may be made available for retrieval over the internet. These images retrieved from the depository are used in the subsequent steps.

Figure 7:
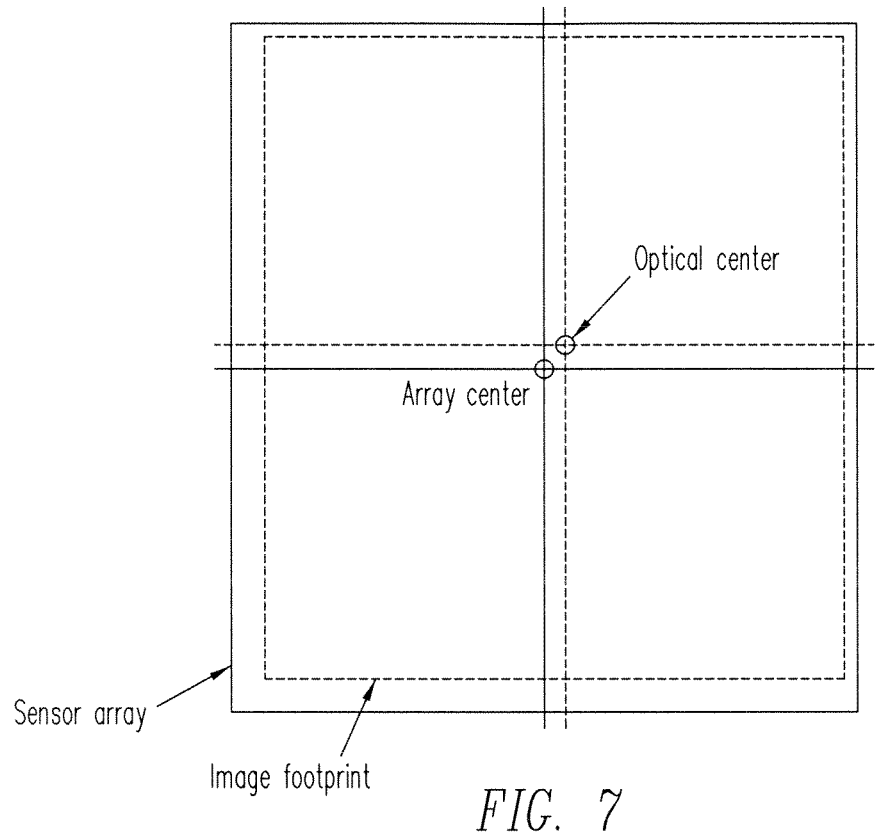
FIG. 7 illustrates the alignment between an image sensor array and the footprint of an image produced by an optical system, such as the lens system of a capsule camera.

FIG. 7 illustrates the alignment between an image sensor array (e.g., sensor array 16) and the footprint of an image produced by an optical system, such as lens 14 of capsule camera 01 of FIG. 1. Ideally, as shown in FIG. 7, if all the components are defect-free and are perfectly aligned, the optical center of a captured image coincides perfectly with the center of the sensor array. In practice, however, the center of the captured image and the center of the sensor array are not perfectly aligned. In addition, imperfections typically exist in the components of the optical system. Normally, the captured image is designed to be slightly smaller than the size of the sensor array to ensure that the entire image is captured within the sensor array. Using the test images for characterization discussed above, a misalignment of the captured image and the center of the sensory array may be derived. For example, under uniform lighting, the average value of a color component in each column of the sensor array indicates where the edges of the captured image are (e.g., scanning from left to right, the column on the right at which the intensity transitions from dark to light, and the column on the left where the image transitions from light to dark). The same procedure along the rows indicates where the edges are at the top and at the bottom of the image.

As another example, when a test image consists of a repetitive pattern, a DCT—such that used in JPEG or MPEG processing—may be used to calculate the frequency-domain image information. The image footprint is located at where the DCT values increase abruptly, corresponding to the positions at which the pattern becomes clear and discernible. An offset between the optical center and the center of the sensor array (e.g., the displacement expressed in x- and y-coordinates) may be stored for later reference in registers or in the non-volatile memory (e.g., archival memory 20). By cropping the operational boundaries of the sensor array to the actual image footprint, or a "meaningful" portion of the image footprint (i.e., the area where the actual field of view is expected), power is not wasted on the areas in the sensor array outside of the actual useful field of view. In addition, the space required for storing the image, or the bandwidth required for transmitting the image, is also reduced. The workstation utilization rate is enhanced and archiving management is also made easier.

The DCT may be performed in 8×8 blocks for luminance. Therefore, in one embodiment, to process an area of M columns of pixels, $$\left(\frac{M}{8}+1\right)$$

blocks are used for each row. Under such an arrangement, the resolution is 8 pixels in both row and column directions. Once an 8×8 block is found where its 64 DCT values start to increase or decrease over previous blocks, the current 8×8 block is reformed by including the last column of the previous block in the same row, and a new DCT value is computed. If the DCT value increases or decreases further still, the procedure is repeated to include one further column of that previous block. This procedure is repeated until the maximum or minimum DCT value is found, representing where DCT values start to increase or decrease in the row direction. When applied in the column direction, this method locates the pixel at which DCT values start to increase or decrease in the column direction.

In another example, the edge information may be used to provide the alignment information. Edge enhancement is used in many of today's commercial cameras or image post processing software. One way to extract an edge is to find the difference in luminance between pixels in adjacent columns. The difference provides edge information in one direction. The same procedure may be used on corresponding pixels in adjacent rows to get edge information in the direction to the columns. The edges obtained for the column and row directions may be used together.

Illustrated also in FIG. 7 is the fact that, due to individual variations in the lens, the magnification factor for each lens is not the same across capsule cameras, thereby resulting in different footprints from camera to camera. An alternative representation of the image footprint may be, for example, two vertices of the rectangular image footprint. As discussed above, image compensation may be carried out within the capsule camera (e.g., image processor 18, or by controlling the sensor analog gain and providing an offset to each color components of every pixel.) The storage space required for compensation or characterization parameter values may be provided in a separate nonvolatile flash memory, in a memory provided in an application-specific integrated circuit (ASIC) or in the image sensor. Alternatively, the compensation or characterization parameter values may also be stored in the same flash non-volatile storage for captured image data (e.g., archival memory 20).

Figure 8B:
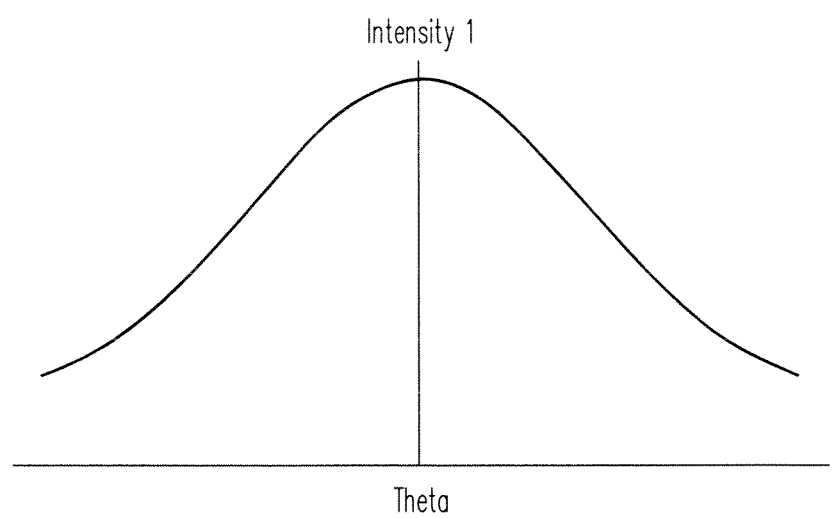
FIG. 8A shows a Lambertian curve of a radiation pattern of an LED (i.e., angle versus illuminance) and FIG. 8B the luminance of LED versus angle.
Figure 8A:
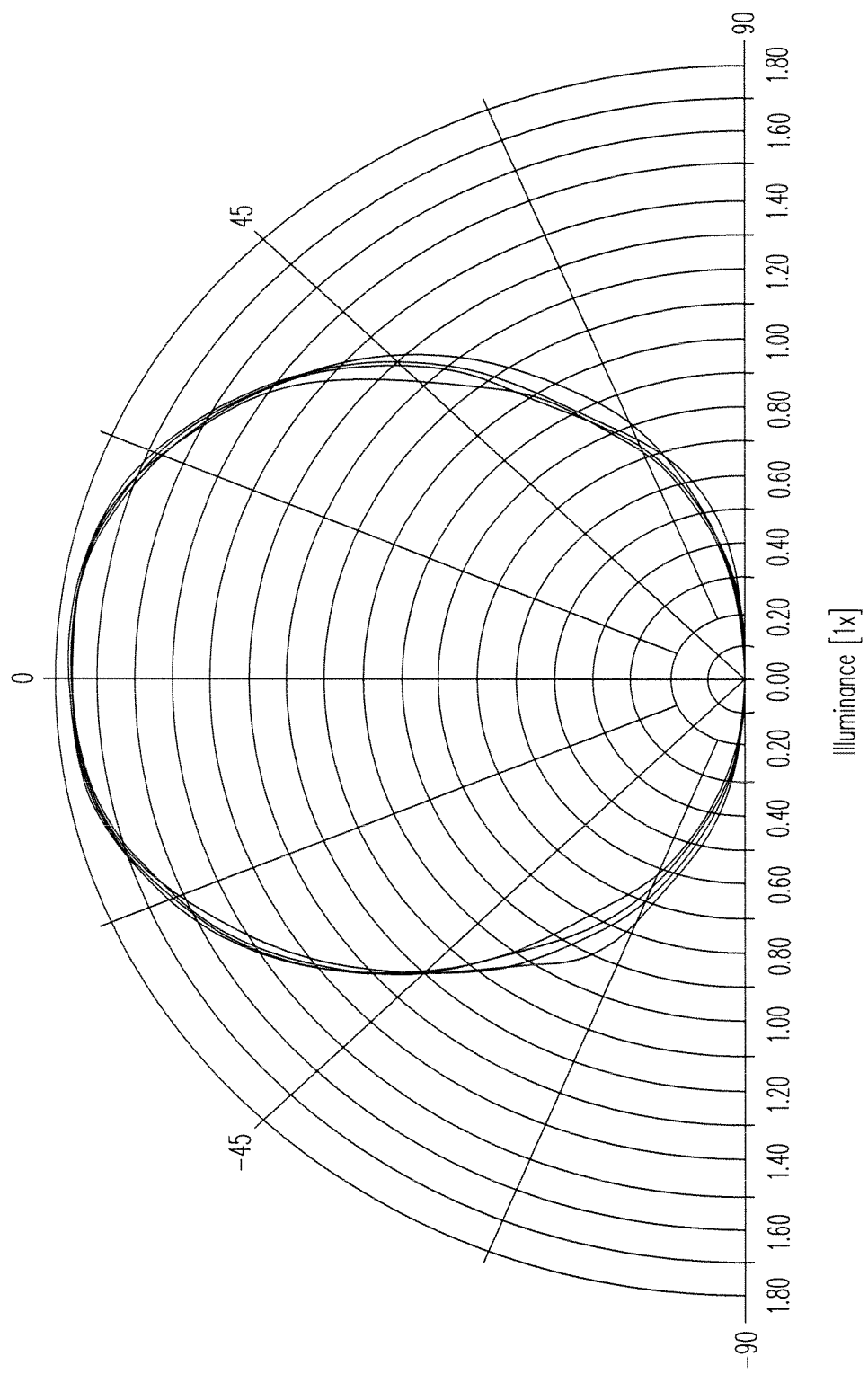

FIG. 8A shows a Lambertian curve of a radiation pattern of an LED (a polar plot showing illuminance as a function angle relative to an axis of the LED) and FIG. 8B the luminance as a function of the angle (linear scale). These figures show the imperfections of an actual LED design.

Figure 9:
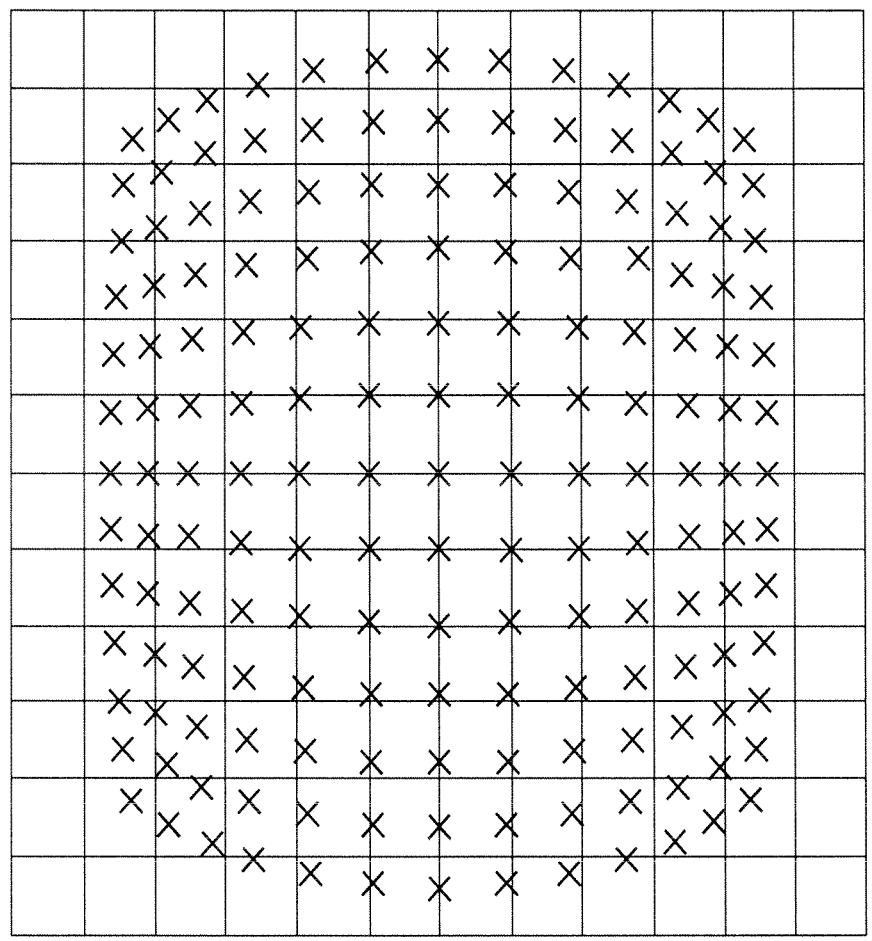
FIG. 9 shows a grid-distortion plot of a lens.

FIG. 9 shows a grid-distortion plot of a lens. As shown in FIG. 9, the distortion in the middle is minimal (i.e., the actual grid points match well with the reference grid) but the distortion becomes pronounced away from the center.

There is a fundamental difference between the design issues posed by FIGS. 8A and 8B and FIG. 9, as large manufacturing variations exist among the LED products. Alternatively, in lens manufacturing, as measured by grid distortion, variations are small and deterministic. The problem shown in FIG. 9 may be compensated in the most part, even after data acquisition by just inverse mapping of the acquired image on the work station or another computer before displaying. The imperfections in FIGS. 8A and 8B are caused by both design imperfections and manufacturing variations. Such imperfection or variations may be efficiently handled using the methods in FIG. 2-6 above.

In one embodiment, the grid distortion could be compensated using the methods in FIG. 2-6 by imaging a known pattern, for example a grid, and detecting an edge (as previously described) to calculate the degree of distortion of the image on the sensor surface caused by optical imperfections (design imperfection as well as manufacturing variations) before displaying. Other problems (e.g., lateral color) may be solved similarly. If deterministic, the image may be compensated on a work station before the image is displayed, and if the defects are caused by both by design imperfection and manufacturing variations, only the methods in FIG. 2-6 may be used realistically to compensate to get a higher fidelity of image arid higher detection rate in case of medical device application.

Accurate reproduction of the captured image is also important. Techniques similar to those described above may be applied to all display devices, including television sets. In recent years, the display industry has increased image resolution from standard definition (SD) to high definition (HD) and ultra-high definition (UHD), and other image resolutions. In addition to increases in resolution, display devices also have their color resolution improved from 8 bits to 9 bits, and even 10 bits, per color component. Thus, the need to control manufacturing variations has increased significantly and, consequently, the cost for ensure display quality has also significantly increased.

According to one aspect of the present invention, to provide a calibration of a display device, standardized color patterns designed for the entire range of displayable colors are provided as images for display on the display device under controlled operating conditions. This step may take place as a manufacturing step, or repeated at a subsequent time when necessary. In many display devices, their accuracy in color/intensity reproduction varies with the operating temperature. Where the color/intensity reproduction accuracy varies with the operating temperature, the calibration may take into account the operating temperature as an operating condition. To take into account of the operating temperature, the display device preferably includes a thermometer configured to measure the operating temperature of the display panel.

During calibration, a diagnostic system detects the intensity of each color component in each pixel of the image displayed on the display device. The diagnostic system includes sensors (e.g., photodiodes, filters) for determining the colors and the intensities of each pixel over a range of operating ranges. At each calibration operating point, the intensity of each color component in each pixel is compared against its corresponding expected value to determine a difference, if any. The diagnostic system may then provide corrective data based on the measured differences. The corrective data may be, for example, in the form of a compensation value to the input value of each color component necessary for achieving the desired color and intensity. The corrective data is then recorded in a nonvolatile memory, so as to allow the necessary correction to each pixel to be made in future display operations.

According to one embodiment of the present invention, the display device may be provided means for measuring temperature ("thermometer", such as a thermal couple). The operating temperature may be considered an operating parameter. Typically, the operating temperature in a display device is higher than the ambient, depending on the display device's power consumption, thermal resistance and ambient temperature and air flow. Compensation that takes into account of the operating temperature may be desirable in some display device.

According to one embodiment of the present invention, the corrective data may be stored in non-volatile memory in any suitable format. For example, the necessary compensation value for each color component of each pixel over entire ranges of input values and operating temperatures may be provided in a table form. Prior to displaying an image, the table is accessed for each color component of each pixel, using the input value and the measured operating temperature. The compensation value thus obtained—after interpolation or extrapolation, if necessary—is added to corresponding input value to prepare the image to be displayed. Alternatively, according to one embodiment of the present invention, after curve-fitting the corrective data to one or more corrective models, such as a linear or polynomial functions of the input value and temperature, the model parameters (e.g., offsets and coefficients of a polynomial function) are then stored in the non-volatile memory. In such a case, prior to displaying the image, the display device computes a compensation value for each color component of each pixel based on the corresponding input value and the operating temperature. The image is then displayed after adjusting each input value based on the computed compensation value.

Many variations of the above approaches are available. For example, a trade-off that reduces the memory requirement for storing the corrective data is available by storing the corrective data, rather than on a per-pixel basis, on the basis of groups of neighboring pixels. According to that format, using the group-specific corrective data, compensation is provided for each pixel. For example, each pixel may be compensated by an amount that is derived from the stored corrective data based on a weighted average of the input values. If corrective data is stored on a group-specific basis, in some display devices, it may be advantageous to take into account high contrast condition with the group of pixels (e.g., an edge with a transition of brightness) in determining compensation for each pixel. In another variation, the input value of each color component and temperature is used to look-up a corrected value. The compensation is applied by displaying the image using the corrected values thus obtained, replacing the input values.

Another approach would be a hybrid form of table look-up and interpolation or extrapolation techniques. For example, the corrective data may be stored in the form of a table of corrected values for selected input ranges and selected temperature ranges, together with values of the model parameters. In such a case, the actual corrected value for each color component can be computed from interpolation or extrapolation from the values obtained from the table using the model parameter values.

Figure 10:
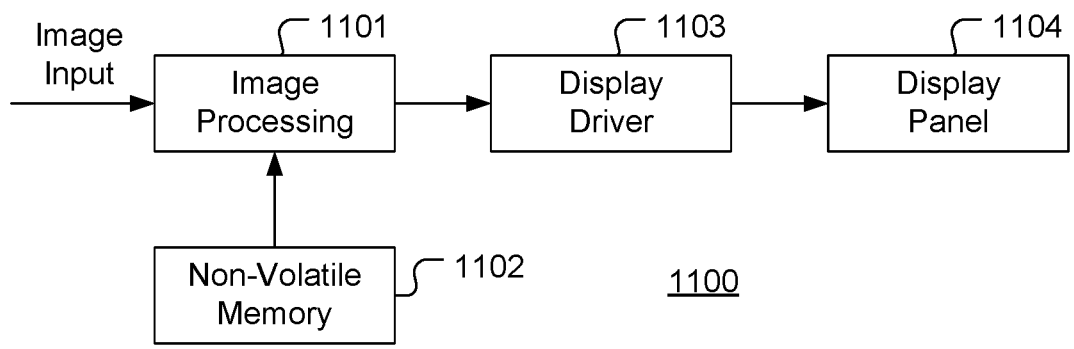
FIG. 10 shows the structures in display 1100 provided for compensating pixel values in the digital domain, according to one embodiment of the present invention.

Compensation can be carried out in the digital or the analog domain. For example, FIG. 10 shows the structures in display device 1100 provided for compensating pixel values in the digital domain, according to one embodiment of the present invention. As shown in FIG. 10, input values for an image to be displayed is received into image processing unit 1101, which retrieves the corrective data or parameters from non-volatile memory 1102. Image processing unit 1101 then computes—if necessary—and applies compensation necessary to each color component of each pixel of the image. The resulting corrected data is then provided to display driver 1103, which provides the control and data signals of display hardware 1104.

Figure 11:
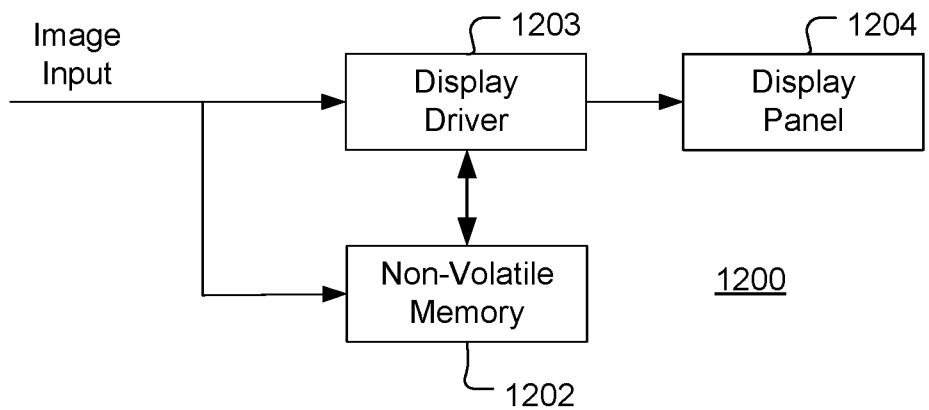
FIG. 11 shows the structures in display 1200 provided for compensating pixel values in the analog domain, according to one embodiment of the present invention.

Alternatively, FIG. 11 shows the structures in display device 1200 provided for compensating pixel values in the analog domain, according to one embodiment of the present invention. As shown in FIG. 11, after conventional image processing, input values for an image to be displayed are provided to display driver unit 1203—which may contain both digital and analog circuits—and non-volatile memory 1202. The input values are used to retrieve corrective data from non-volatile memory 1202. Display driver unit 1203 then applies compensation (e.g., adjusts the gain and offset at each pixel) necessary to accurately reproduce each color component of each pixel of the image to the desired value. Based on the corrected values, the display driver unit 1203 provides control and data signals to display hardware 1204.

According to one embodiment of the present invention, rather than providing the compensation in the display device itself, another device (e.g., a computer or a set-top box providing the image data to the display device) may perform the compensation on the image data before providing the compensated image data to the display device. In that embodiment, the device performing the compensation retrieves the corrective data from a non-volatile memory of the display device.

The above detailed description is provided to illustrate the specific embodiments of the present invention and is not intended to be limiting. Numerous variations and modifications within the scope of the present invention are possible. The present invention is set forth in the accompanying claims.

We claim:

1. A display system for displaying input image data of an image received, the display system comprising:
   display hardware for displaying the image, wherein the display hardware comprises a plurality of display pixels and a thermometer that measures an operating temperature at the plurality of display pixels of the display hardware;
   a non-volatile memory for storing corrective data derived for the display hardware, wherein the corrective data are used for compensating manufacturing variations between the plurality of display pixels of the display hardware, and wherein the corrective data are derived based on differences between detected intensities of each color component for standardized color patterns input in the plurality of display pixels and corresponding expected values of each color component for the standardized color patterns input in the plurality of display pixels respectively; and
   an image processing circuit for applying the corrective data to the input image data based on measured operating temperature at the plurality of display pixels of the display hardware to generate corrected data signals for displaying the image in the display hardware.

2. The display system of claim 1, wherein the corrective data in the non-volatile memory are generated from a calibration step during manufacturing by a diagnostic system detecting an intensity of each color component in each pixel of the display hardware.

3. The display system of claim 2, wherein the corrective data are stored in the non-volatile memory to enable compensation to the input image data over a range of intensities for each color component of each pixel.

4. The display system of claim 1, wherein the corrective data are stored in the non-volatile memory in a table format.

5. The display system of claim 1, wherein the corrective data correspond to corrected values for replacing corresponding values in the input image data.

6. The display system of claim 1, wherein the corrective data correspond to compensation values to be applied to corresponding values in the input image data.

7. The display system of claim 1, wherein the corrective data correspond to corrective values for predetermined values in the input image data, and wherein the corrective values for the input image data are interpolated or extrapolated from the corrective values for the predetermined values.

8. The display system of claim 1, wherein the corrective data correct one or more predetermined parameter values in the input image data.

9. The display system of claim 1, wherein the corrective data correspond to values of parameters of a model from which corrective values are generated based on the input image data.

10. The display system of claim 9, wherein the model comprises a linear function or polynomial function.

11. The display system of claim 1, wherein the corrective data comprise corrective values applicable to neighboring pixels.

12. The display system of claim 1, wherein the corrective data are applied to the display hardware in a digital domain.

13. The display system of claim 1, wherein the corrective data are applied to the display hardware in an analog domain.

14. A display system for displaying input image data of an image received, the display system comprising:

display hardware for displaying the image, wherein the display hardware comprises a plurality of display pixels;

a non-volatile memory for storing corrective data derived for the display hardware, wherein the corrective data are used for compensating manufacturing variations between the plurality of display pixels of the display hardware, and wherein the corrective data are derived based on differences between detected intensities of each color component for standardized color patterns input in the plurality of display pixels and corresponding expected values of each color component for the standardized color patterns input in the plurality of display pixels respectively; and an image processing circuit for applying the corrective data to the input image data to generate corrected data signals for displaying the image in the display hardware.

15. The display system of claim 14, wherein the corrective data in the non-volatile memory is generated from a calibration step during manufacturing by a diagnostic system detecting an intensity of each color component in each pixel.

16. The display system of claim 14, wherein the corrective data stored in the non-volatile memory enable compensation to the input image data over a range of intensities for each color component of each pixel.

17. The display system of claim 14, wherein the display hardware further comprises a thermometer for measuring an operating temperature in the display hardware, and wherein the corrective data are applied to the input image data based in part on the measured temperature.

18. The display system of claim 14, wherein the corrective data are stored in the non-volatile memory in a table format.

19. The display system of claim 14, wherein the corrective data correspond to corrective values for predetermined values in the input image data, and wherein the corrective values for received input image data are interpolated or extrapolated from the corrective values for the predetermined values.

20. The display system of claim 14, wherein the corrective data correct one or more predetermined parameter values of input image data.

21. The display system of claim 14, wherein each pixel is corrected based on a function of the input image data and the function comprises a linear function or polynomial function.

* * * * *